US008852669B2

(12) United States Patent
Vogt et al.

(10) Patent No.: US 8,852,669 B2
(45) Date of Patent: Oct. 7, 2014

(54) COATING METHOD AND COATING DEVICE FOR MEDICAL IMPLANTS

(71) Applicant: Heraeus Medical GmbH, Wehrheim (DE)

(72) Inventors: Sebastian Vogt, Erfurt (DE); Ekaterini Copanaki, Frankfurt (DE); Sebastian Gaiser, Frankfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 13/666,553

(22) Filed: Nov. 1, 2012

(65) Prior Publication Data
US 2013/0122184 A1    May 16, 2013

(30) Foreign Application Priority Data
Nov. 3, 2011    (DE) .......................... 10 2011 117 526

(51) Int. Cl.
| B05C 11/00 | (2006.01) |
| B05D 3/00 | (2006.01) |
| B05D 1/28 | (2006.01) |
| B05C 1/06 | (2006.01) |
| B05D 1/24 | (2006.01) |

(52) U.S. Cl.
CPC ... *B05D 1/28* (2013.01); *B05D 1/24* (2013.01); *B05C 1/06* (2013.01)
USPC ........ 427/2.24; 427/2.25; 427/2.26; 427/429; 118/266; 118/268; 118/270; 451/127; 215/220

(58) Field of Classification Search
None
See application file for complete search history.

(56) References Cited

U.S. PATENT DOCUMENTS

| 3,003,461 | A | * | 10/1961 | Rosenthal ...................... 118/266 |
| 3,357,395 | A | * | 12/1967 | Lorber .......................... 118/266 |
| 5,607,685 | A | | 3/1997 | Cimbollek et al. |
| 6,248,085 | B1 | * | 6/2001 | Scholz et al. ..................... 604/2 |
| 7,563,324 | B1 | * | 7/2009 | Chen et al. .................... 118/270 |

(Continued)

FOREIGN PATENT DOCUMENTS

| DE | 4404018 A1 | 8/1995 |
| DE | 10142465 A1 | 7/2003 |

(Continued)

OTHER PUBLICATIONS

Australian Examination Report for corresponding Australian Patent Application No. AU 2012244142 dated Apr. 15, 2013.

(Continued)

*Primary Examiner* — Cachet Sellman
(74) *Attorney, Agent, or Firm* — Norris McLaughlin & Marcus, P.A.

(57) ABSTRACT

Methods and devices coat, at least regions of, a medical implant, preferably of an artificial joint or a fixation for a joint. The method provides a medical implant, fills a device with a liquid having at least one pharmaceutically active substance, wherein the device has a compressed, at least over regions thereof, elastic, porous transfer means increases a volume of the transfer means, whereby the liquid is taken up at least partly into the pores of the transfer means, and transfers the liquid from the transfer means to a medical implant surface to be coated. The device coats, at least regions of, a medical implant, by means of the method, whereby the device has a compressed, at least over regions thereof, elastic, porous transfer means.

22 Claims, 4 Drawing Sheets

(56) References Cited

U.S. PATENT DOCUMENTS

| | | | |
|---|---|---|---|
| 7,976,891 B1* | 7/2011 | Van Sciver et al. | 427/2.24 |
| 2004/0062592 A1 | 4/2004 | Shekalim et al. | |
| 2005/0074544 A1 | 4/2005 | Pacetti et al. | |
| 2007/0125247 A1 | 6/2007 | Kunstmann et al. | |
| 2011/0287169 A1 | 11/2011 | Hoffmann et al. | |
| 2012/0164310 A1* | 6/2012 | Vogt et al. | 427/2.24 |

FOREIGN PATENT DOCUMENTS

| | | | |
|---|---|---|---|
| DE | 102010055559 A1 | 6/2012 | |
| EP | 0623349 A1 | 11/1994 | |
| EP | 1374923 A2 | 1/2004 | |
| EP | 1470829 A1 | 10/2004 | |
| EP | 2468315 A1 | 6/2012 | |
| WO | 2008/086794 A2 | 7/2008 | |

OTHER PUBLICATIONS

European Search Report dated Mar. 15, 2013, for corresponding EP 12007168.3-1363.

German Office Action for corresponding German Patent Application (DE 10 2011 117 526.5) dated Jul. 17, 2012.

Chinese Office Action for corresponding Chinese Patent Application No. 201210432471.0 dated Apr. 1, 2014.

* cited by examiner

COATING METHOD AND COATING DEVICE FOR MEDICAL IMPLANTS

The invention relates to a method for coating, at least regions of, a medical implant, preferably of an artificial joint or a fixation for a joint.

The invention also relates to a device for coating, at least regions of, a medical implant using said method.

The coating of medical implants with pharmaceutical agents has garnered increasing attention in recent years. Antibiotic protection of the surface of implant materials is a main application of coating methods in this context. In addition, coating with growth factors, coagulation factors, bisphosphonates, anaesthetics, proteins, peptides, hormones, and other agents is also of interest.

Any implantation of articular endoprostheses, and of osteosynthesis materials as well, is associated with a certain risk of microbial contamination. Successful colonisation of microbial pathogens on the surface of the implant can lead to the manifestation of post-operative osteitis/osteomyelitis. Osteitis/osteomyelitis is a severe complication for the patient and, in addition, is associated with substantial costs.

Gentamicin-doped PMMA bone cement has been in clinical use with cemented articular endoprostheses for decades with much success. The broadband antibiotic, gentamicin, contained in the bone cement protects the surface of the bone cement effectively from bacterial infections.

With regard to non-cemented articular endoprostheses and osteosynthesis materials, a number of approaches has been proposed in order to also attain local antibiotic protection of the implant surfaces.

For example, the use of poorly water-soluble salts of antibiotics has been described in several patent specifications. For exemplary purposes, EP 0 623 349 A1, EP 1 470 829 A1, EP 1 374 923 A2, DE 101 42 465 A1, and DE 44 04 018 A1 can be cited in this context. Said poorly water-soluble salts dissolve while releasing the antibiotics contained therein as a result of the action of body fluids. Prolonged release of the agent is advantageous. However, the laborious production of said salts is disadvantageous.

Alternatively, it is feasible to use water-soluble antibiotic salts. This is associated with a problem related to fixation of the antibiotic on the implant surface.

The majority of coatings that have been described thus far is preferably intended for the manufacture of coated implants under industrial conditions. This means that the industrial coating of said implants can only involve few agents that are relevant for large-scale use in order to be able to guarantee that the industrial manufacture is economic through sufficiently large throughput.

In particular in the case of antibiotic coatings, though, considering the increasingly problematic resistance status and the ensuing increased manifestation of multi-resistant pathogens, such as MRSA and MRSE, it is of interest to use antibiotics or combinations of antibiotics, which are specifically adapted to the germ at hand, for the coating of revision prostheses in one-stage or two-stage septic articular endoprosthesis replacement in order to ensure effective initial antibiotic protection of the implant surfaces.

This is disadvantageous in that the methods for coating the medical implants are relatively laborious. Variable short-term application is not feasible. Various scenarios then necessitate the stock-keeping of various coated medical implants in order to meet the needs of the different patients. This requires extensive stock-keeping and prevents uncommon solutions for specific cases.

DE 10 2010 055 559, which was not pre-published, relates to a coating method and a coating device, in which a transfer means is used in a vessel, whereby the transfer means is soaked before a medical implant is coated with a liquid containing at least one pharmaceutically active substance before a medical implant is coated. This is disadvantageous in that a large quantity of said liquid needs to be placed in the vessel for the transfer means to be well-filled. This relates, in particular, to liquids showing no strong adhesion to the surface of the transfer means or liquids containing very expensive substances or substances that might contaminate the environment and/or, in particular, the operating theatre.

Accordingly, it is the object of the invention to overcome the disadvantages of the prior art. In particular, a simple and easy-to-use method and a device are to be provided for this purpose that can be used to coat a medical prosthesis without interfering with an ongoing surgery (OR). The aim is to be able to coat as many different medical implants as possible using the same method and the same device. Moreover, the method and the device should be variable to use such that they can be adapted to the medical needs, in particular to a suitable medication for the patient. The cleanliness required in operating theatres is another factor to take into account. Moreover, the environment and the often valuable resources are to be protected.

It is also an object of the invention to develop a coating method that is as simple as possible and can be used by the OR staff during an ongoing surgery, with the least time expenditure, to coat very different implants from any manufacturers with pharmaceutical preparations. Moreover, it is an object of the invention to develop a simple coating device that allows the OR staff to coat implants under OR conditions with the smallest effort possible using any liquid or flowable pharmaceutical preparations such as liquids or suspensions. Moreover, the device is to be designed such that, to the extent possible, no spray mist or droplets can contaminate the OR area. Moreover, another object of the invention is to ensure that the method or device does not, to the extent possible, involve the release of plastic particles, metal particles or other particles that can be biodegraded not at all or only partly. Likewise, the release of particles from brushes, paint brushes or other hairs, fibres or bristles is to be prevented. Another object is that the device should, in particular, be suitable for the coating of non-cemented articular endoprostheses and osteosynthesis materials.

The objects of the invention as well as other problems not specified herein are met through a method for coating at least regions of a medical implant, preferably of an artificial joint or a fixation for a joint, in which a medical implant is provided, a liquid comprising at least one pharmaceutically active substance is filled into a device comprising a compressed, at least over regions thereof, elastic, porous transfer means, the volume of the transfer means being increased, whereby the liquid is taken up at least partly into the pores of the transfer means and subsequently the liquid is transferred from the transfer means to a medical implant surface to be coated.

Methods according to the invention are carried out before inserting the medical implants. Accordingly, the methods proceed "ex vivo".

According to the invention, a pharmaceutically active substance shall be understood to mean pharmaceutically effective means or means with a pharmacological effect as well as means that support a pharmacological effect or support in any other way the self-healing forces of the body. Examples include antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

The scope of the invention can also provide that the liquid comprises an aqueous solution of an antibiotic, preferably that an aqueous gentamicin sulfate solution with a gentamicin sulfate content of 10.0 to 88.0% by weight is used, whereby it is particularly preferred to use a gentamicin sulfate solution with a gentamicin sulfate content of 75.0 to 80.0% by weight. Said gentamicin sulfate solution has an oily-viscous consistency and adheres very well to metal surfaces.

In this context, the invention can further provide that common pharmaceutical stabilisers are contained in the gentamicin sulfate solutions. These improve the durability and thus the usability of the liquid to be applied.

The invention can also provide for the use of other aminoglycoside antibiotic solutions such as aqueous solutions of tobramicin sulfate, amikacin sulfate, netilmicin sulfate, and sisomicin sulfate as liquid or components of the liquid. It is also feasible to use aqueous solutions of vancomycin, dalbavancin, ramoplanin, daptomycin, moxifloxacin, clindamycin, and lincomycin.

Moreover, the scope of the invention can provide for the use of combinations of solutions of different antibiotics as liquid. Examples include two-antibiotic combinations of gentamicin sulfate and vancomycin hydrochloride, the two-antibiotic combination of daptomycin and gentamicin sulfate, and the two-antibiotic combination of gentamicin sulfate and clindamycin as well as the three-antibiotic combination of gentamicin sulfate and vancomycin hydrochloride and clindamycin hydrochloride.

The invention can further provide for antiseptics solutions to be used as liquid, in particular solutions of chlorohexidine digluconate, octenidine dihydrochloride, and polyhexanide.

The scope of the invention also includes that the liquid comprises solutions of antibiotics and antiseptic agents that contain, as solvents, organic solvents or combinations of organic solvents or combinations of organic solvents and water. This allows, for example, poorly water-soluble antibiotic salts, such as laurates, myristates, palmitates, and stearates, to be used as well. Moreover, poorly water-soluble antibiotics or antibiotic salts in the form of aqueous suspensions can also be used.

A particularly advantageous refinement of a method according to the invention provides the liquid to be transferred out of the transfer means onto the medical implant surface to be coated.

According to the invention, the pores of the transfer means can be implemented through channels, reservoir chambers, fibres interstices and/or other intervening spaces of the transfer means.

Moreover, it is a particular advantageous for the invention to provide the liquid to be introduced into the transfer means, preferably into pores, channels, reservoir chamber and/or intervening spaces of the transfer means, or the transfer means to be soaked with the liquid, in particular right before its use. This ensures the flexibility of the method.

In this context, the invention can provide a liquid matching the treatment scenario, in particular an antibiotic or mixture of antibiotics matching the treatment scenario, being introduced into the transfer means. Accordingly, a solution that is adapted to the specific needs of a certain patient can be provided shortly before the actual coating of the medical implant.

According to a particularly advantageous and preferred refinement of the method according to the invention, the invention can provide the volume of the transfer means to be increased through relaxation and/or decompression of the transfer means.

This utilises the restoring force of the elastic transfer means to increase the volume of the transfer means. The pores of the transfer means open up along with the increase in the volume of the transfer means. The opening pores soak up the liquid such that the transfer means becomes soaked with liquid.

According to a further refinement, the invention can provide the transfer means to be kept in the compressed state through a compressing facility, whereby the volume of the transfer means is increased by means of the compressing facility by operating the device, in particular the compressing facility.

In this context, the invention can provide that a lid having a thread is used as compressing facility, whereby the thread engages a counter-thread of the device, and that the volume of the transfer means is increased by means of unscrewing the lid.

Said measures generate a simple, inexpensively implemented, and easily operated structure which can be operated easily and safely under the difficult conditions during a surgery.

The invention can also provide the liquid to be filled into the device through at least one feed-through in the device, in particular in the lid of the device, in particular right before transfer to the medical implant, whereby it is preferable for the previously closed feed-through to first be opened, particularly preferably through puncturing a closure membrane.

This renders the method flexibly usable with various liquids.

Another refinement of the invention can provide that the liquid is transferred from the transfer means onto a medical implant surface to be coated by means of pushing the medical implant through one slit or more slits and/or a recess in the transfer means and retracting it again, whereby any excess of liquid is preferably wiped off during retraction.

In this context, the invention can provide the transfer means to be compressed, at least over regions thereof, while the medical implant is pushed through and at least part of the liquid to be squeezed from the transfer means and transferred to the surface of the medical implant, in particular to be transferred to all sides of the surface of the medical implant.

Said simple and easily applied procedural steps again make use of the elasticity of the transfer means as well as of the fact that the volume of the pores of the transfer means decreases upon compression, i.e. upon the action of a force, and the liquid contained in the pores is squeezed from the pores to reach the surface of the transfer means, and be transferred in this location to the medical implant surface to be coated.

The invention can just as well provide for the use of an antibiotic or mixture of antibiotics as liquid, preferably a suspension or a solution, particularly preferably an aqueous solution.

The invention can further provide a powder to be applied to the wetted surface of the medical implant after transfer of the liquid to the medical implant, preferably the medical implant to be dipped into a powder, whereby the powder preferably comprises at least one pharmaceutically active substance. The powder can be contained in a hollow space of the container below the transfer means.

Additional powder coating is advantageous for some medical applications since it allows other medically effective substances that are insoluble or poorly soluble or substances at other concentrations or combinations thereof to be used. After coating with a liquid film, the powder adheres particularly well to the surface of the medical implant.

Another particularly preferred refinement of the invention can provide for the use of a coloured liquid such that the coated region of the medical implant is identified by colour, whereby it is preferable to check the completeness of coating of the region to be coated by means of the colouration.

This allows to ensure, according to the invention, that all regions of the implant have actually been coated.

Particularly advantageous methods are characterised in that the liquid is applied to the medical implant surface to be coated on all sides using a ring-shaped transfer means. This accounts for the specific geometry of many medical implants, in particular of articular prostheses.

In order to prevent contamination of the surroundings by the liquid, the invention can provide the medical implant to be introduced into a container, in which the transfer means is situated, before contacting it with the transfer means, and to be pulled out of the container after transfer of the liquid to the medical implant.

Further improvement can be attained through application of a powder to the wetted surface of the medical implant after transferring the liquid to the medical implant, preferably through dipping the medical implant into a powder, whereby the powder preferably comprises at least one pharmaceutically active substance. A suitable powder can, for example, promote bone growth and thus improve the success of an implantation since the powder effects a more stable connection of the implant to the adjacent bone material to be formed.

The invention can just as well provide the medical implant to be pushed through at least one membrane or at least one membrane to be opened. In this context, the at least one membrane can cover at least regions of the liquid and/or powder and/or the at least one membrane can seal the container. The membrane prevents contamination of the inside of the container, liquid and/or powder prior to its use. Puncturing the membrane ensures that the protective membrane is opened only shortly before the application. For this purpose, the membrane should be structured such that no shreds or other parts of the membrane can become situated on the transfer means or inside the container or adhere to the medical implant.

The risk of possibly contaminating the surroundings can be reduced and the often expensive coating materials can be saved according to the invention in that part of the transferred liquid is wiped off, in particular when the medical implant is pulled out of the container, preferably on a wiper designed for this purpose. This can prevent or at least reduce contamination of the surroundings, i.e. in particular of an OR area, by the liquid and, if applicable, by the powder. This is advisable especially upon the use of antibiotics since it allows the development of resistant pathogens in the OR area to be prevented.

The invention can also provide that the medical implant to be coated is inserted into the device repeatedly or pushed through the transfer means repeatedly.

The invention can also provide for the method to be repeated as often as required for complete coating of the medical implant surface to be coated to be attained. In particular in the context of colouration of the liquid and testing of the completeness of coating through said colouration, this is advantageous according to the invention in order to obtain a sufficiently coated medical implant.

Moreover, the invention can provide that at least 50% of the surface of the medical implant, preferably at least 80%, particularly preferably 90% of the surface of the medical implant, are being coated.

A particularly advantageous refinement of the method is characterised in that non-cemented hip endoprostheses, shoulder endoprostheses, elbow prostheses, marrow nails or osteosynthesis plates are used as medical implant.

The objects of the invention as well as further problems not mentioned here are also met and solved through a device for coating at least regions of a medical implant, in particular through a method of this type, whereby the device comprises at least one transfer means that is, at least over regions thereof, compressed, elastic, and porous.

Particularly preferably, the device is a medical coating device for medical implants. Any reference to a device made herein according to the invention can be a reference, according to the invention, to a medical coating device for medical implants of this type.

In this context, the invention can provide the device to comprise a compressing facility, whereby the transfer means can be kept in a compressed state by means of the compressing facility and the volume of the transfer means can be increased preferably through operating the device, in particular through operating the compressing facility.

As before, the invention can provide the compressing facility to be a lid having a thread that is screwed into the device, whereby the volume of the transfer means can be increased through rotating and/or unscrewing the lid.

It can be advantageous in this context to provide that the lid comprises a feed-through through which a liquid can be introduced into the inside of the device in the region of the transfer means, whereby the feed-through preferably opens into a distributing facility by means of which the liquid can be distributed over at least regions of the surface of the transfer means, and the distributing facility particularly preferably comprises ribs in a radial arrangement.

According to another refinement, the invention provides a mobile support ring to be arranged between the compressing facility and the transfer means and to support the at least one transfer means on the inside of the device, in particular independent of the compression of the transfer means, whereby the support ring preferably comprises a locking device which uses the limit stop of the device to support the inserted support ring, and thus the transfer means, in the device, particularly preferably limits the motion of the support ring in the device.

Another refinement of the invention can provide the transfer means to be arranged in a container comprising an opening for introduction and removal of the medical implant, whereby the opening preferably is closed through the lid.

A refinement of the invention that is particularly preferred according to the invention can be implemented in that the device comprises a wiper that is preferably arranged in the region of the opening, in particular between the opening and the transfer means.

The wiper can be used to wipe excess liquid off the medical implant when the medical implant is being retracted from the device.

In this context, the invention can provide the wiper to be disc-shaped and to comprise at least one notch that connects the top and the bottom of the disc.

Alternatively, the invention can provide the wiper to be shaped like an envelope of cone or a hemispherical surface, whereby the tip of the cone or the hemisphere is oriented towards the transfer means and the cone or the hemisphere preferably contain at least one notch that connects the top and the bottom of the wiper. Through this means, any droplet or particles that might detach from the transfer means during retraction of the implant can be hurled about only in such manner that they hit the internal wall of the container and hit the underside of the wiper such that contamination of the surroundings by the liquid is thus prevented.

Moreover, the invention can provide the transfer means to comprise at least one notch, preferably multiple transfer means to each comprise at least one notch, whereby the arrangement of the transfer means with respect to each other is such that the notches are arranged offset with respect to each other.

This supports or ensures coating of the medical implant on all sides.

Another refinement of the invention can provide the one transfer means to be a sponge or the multiple transfer means to be sponges that can be used to transfer the liquid to the medical implant surface to be coated, whereby the sponge or sponges preferably is or are manufactured from a material having a hydrophilic surface, whereby particularly preferably at least one other part of the device, in particular the wiper, is manufactured from a hydrophobic material.

Moreover, the invention can provide a hollow space to be arranged below the transfer means, whereby the transfer means preferably is arranged on a membrane that can be punctured and closes the inside of the hollow space.

The invention can provide the transfer means to be arranged in a container comprising an opening for introducing and taking out the medical implant. The purpose of the container is to prevent inadvertent splashing and dripping of the liquid in the surroundings.

In this context, the invention can again provide the opening to be closed through a lid. This allows contamination of the content prior to the use of the device to be prevented.

Particularly advantageous devices are characterised in that the transfer means comprises pores and in that the liquid can be taken up into and/or is contained in the pores of the transfer means, preferably in the form of a solution and/or suspension.

A particularly preferred refinement of the invention provides the pharmaceutically active substance to contain antibiotics and/or organic antiseptic agents in a manner such that the coating to be generated contains a pharmaceutically active dose.

Moreover, the invention can provide the device to comprise a vacuum connection that can be connected to a vacuum source and is preferably arranged between the wiper and the transfer means. This can ensure, in addition, through the aspiration of possible droplets of the liquid and/or suspension that no contamination of the surroundings by pharmaceutical agents occurs.

According to a refinement, the invention can provide the transfer means to be manufactured from a hydrophilic material and preferably at least one other part, in particular the container and/or the wiper, to be manufactured from a hydrophobic material. It is preferable to use aqueous solutions and/or suspensions of pharmaceutical agents for coating. Provided the transfer means is manufactured from a hydrophilic material, aqueous solutions and/or suspensions are preferably situated in the porous hydrophilic material, rather than on the hydrophobic surface of the container and of the wiper. This behaviour allows coating devices pre-filled with aqueous solutions and/or suspensions to get by with even the least volumes of said aqueous solutions or suspensions and still allow for assured coating.

The invention can also provide for the wiper to be made of a biocompatible elastomer, thermoplastic material, a metal foil or composites that are manufactured from metal-elastomer combinations or metal-plastics combinations.

Another refinement of the invention provides the wiper as a ring that contains bristles that are arranged to be radial with respect to the centre of the container and, if applicable, can form a cone whose tip is arranged in the direction of the transfer means. Said bristles can be made of plastic material, whereby the bristles should be sufficiently strong and be anchored sufficiently strongly for said bristles not to become detached or break off, if at all possible.

The invention can also provide the wiper as rollers and/or spheres that are connected to the container through elastic connecting means.

Furthermore, the invention can provide that at least one notch connects the upper side of the transfer means to the underside of the transfer means. The medical implant can be plugged or pushed through the transfer means through said at least one notch.

It is particularly advantageous in this context to have radial notches formed in the transfer means.

The invention is based on the surprising finding that a liquid for coating a medical implant before an surgery can be soaked up through a decompressing transfer means easily, rapidly, and without contaminating the surgical environment. The transfer means thus gets filled with the liquid while the transfer means expands and is in contact with the liquid. The liquid can then be transferred easily to the surface of the medical implant by means of the liquid-soaked transfer means. The liquid can be filled into the device right before application. Accordingly, this application enables a coating during or shortly before a surgery. This allows the coatings to be better adapted to the individual needs of the patients, and the use of pharmaceutically effective substances with shorter half-lives is enabled as well. Moreover, the splashing of the liquid is reduced and thus contamination of the surroundings is prevented. This is important especially for use in an operating theatre.

The transfer means, which preferably is a sponge, can be filled rapidly and efficiently by means of the relaxation or expansion of the transfer means.

Thus is provided a method according to the invention for rapid and simple coating of medical implants with pharmaceutical preparations under OR conditions. Moreover, many refinements according to the invention achieve that the release of droplets or splashes of agent in the OR area is largely prevented. The coating device is designed in particular for the inexpensive coating with pharmaceutical agents of non-cemented articular endoprostheses, non-cemented revision articular endoprostheses and osteosynthesis material.

Accordingly, rather than coating the medical implant in advance during its manufacture, it can also be coated right before inserting it using assessable quantities of a pharmaceutically active substance. This allows coatings with a relatively service life to be used as well. Moreover, even a layer that is still liquid can be used, which opens up new application fields and renders new agents accessible.

The unfilled device can be filled with an agent solution or agent suspension containing one or more pharmaceutical agents right in the operating theatre. In the case of the antibiotic coating, this enables suitable selection of an antibiotic or combination of antibiotics based on the existing resistance status and thus ensures that the coating matches the antibiotic sensitivity pattern.

It is also feasible to fill non-pre-filled devices with suitable solutions or suspensions of agents in the respective hospital pharmacy prior to a surgery such that the coating can be carried out during the surgery without any time delay.

According to the invention, it is particularly suitable in this context to use as pharmaceutically active substance a pharmaceutical agent such as, for example, antibiotics, organic antiseptic agents, copper salts, copper oxide, gallium salts, strontium salts, lithium salts, silver salts, silver oxide, bisphosphonates, growth factors, steroid hormones, non-steroidal hormones, hemostyptic agents, antiphlogistic agents, plasmids, cosmids, linear DNA, and mixtures thereof.

For initial antibiotic protection, it is sufficient to have sufficiently high concentration(s) of antibiotic or antibiotics at the implant surfaces for a period of 24 to 72 hours. Therefore, sufficient temporary local antibiotic protection of the medical implant can be attained even upon local introduction of simple water-soluble antibiotics.

The device can be provided as drug or as medical product.

A combination of the device according to the invention and a medical implant could be offered as well. Said combination is formed by the device and the implant, whereby said combination has a minimal service life of 0.1 seconds. The combination is generated during the coating process.

The scope of the invention also includes a medical coating device for coating medical implants with liquid pharmaceutical preparations, comprising a hollow body with one open and one closed end and at least one of the following features:
A) at least one elastic, open-porous transfer means that is arranged at the open end of the hollow body;
B) at least one support for the transfer means on the inside of the hollow body;
C) at least one membrane closing the underside of the elastic, open-porous transfer means in the direction of the inside of the hollow body;
D) at least one guide ring blocking the transfer means in the direction of the open end of the hollow body;
E) at least one wiper;
F) one internal thread or at least one thread section of an internal thread on the open end of the hollow body; and/or
G) a screw lid that comprises at least one external thread and has ribs or fins arranged on its underside, whereby the surfaces between the ribs or fins are connected through at least one opening connecting the upper side of the screw lid to the underside.

It is preferred in feature combination G) that the total volume of the hollow spaces between the ribs or fins on the underside of the screw lid and of the hollow body arranged on the backside of the screw lid to be smaller than or equal to the total pore volume of the elastic, open-porous transfer means.

Preferably, the opening on the upper side of the screw lid in feature combination G) is provided as a hollow body, in particular as a tube.

The rationale underlying the invention is to use an elastic, open-porous transfer means that has a high restoring force upon deformation. Compression of an elastic, open-porous material causes the air present in the pores to exit. When the compression is reduced, the restoring force restores the material to its original volume whereby the pores take up ambient gaseous or liquid medium from while they open up again.

Exemplary embodiments of the invention shall be illustrated in the following on the basis of six schematic figures, though without limiting the scope of the invention. In the figures.

Figure 1:
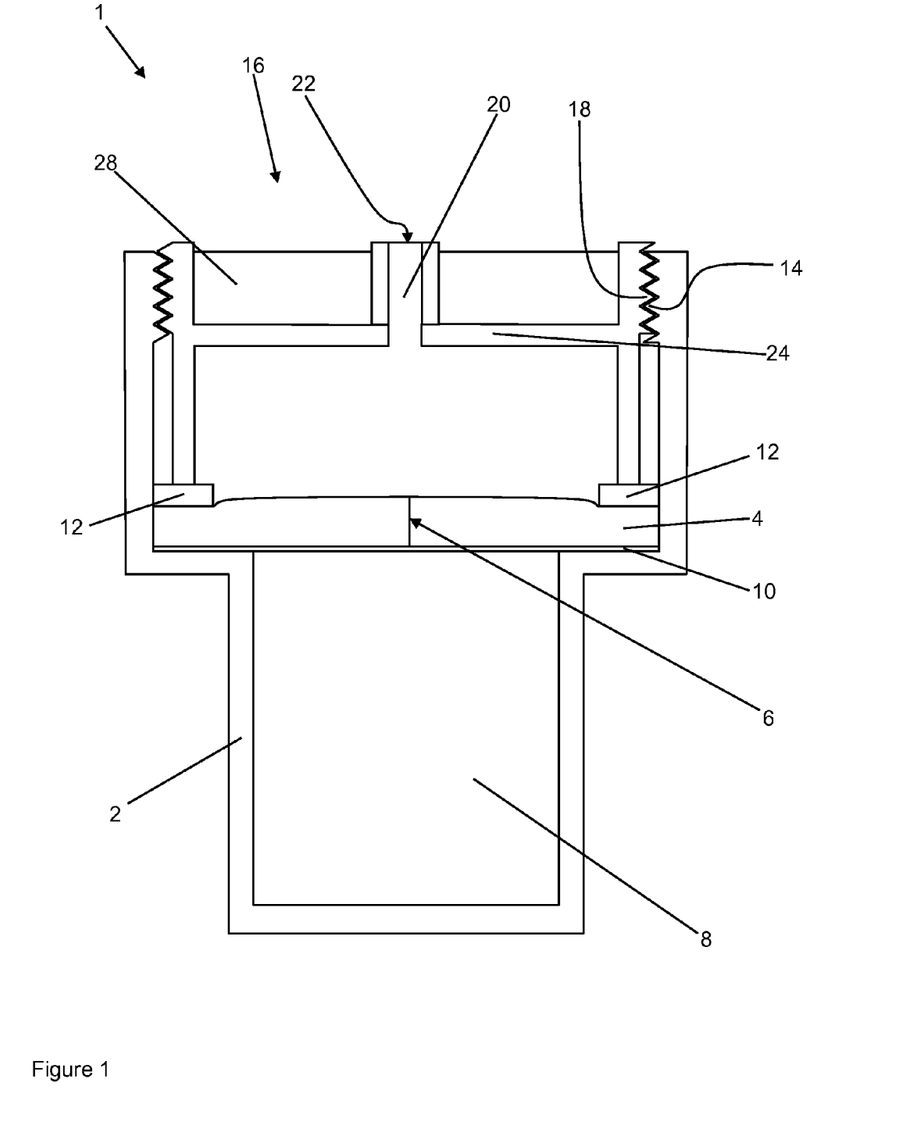
FIG. 1: shows a schematic cross-sectional view of a device according to the invention having a compressed transfer means.

FIG. 1 shows a schematic cross-sectional view of a device 1 according to the invention. The device 1 comprises a container 2 that is open in upward direction. The side walls of the container 2 are cylindrical in shape and of even thickness. The floor and the side walls of the container 2 are manufactured from a hydrophobic material or coated with a hydrophobic layer.

An elastic transfer means 4 is arranged on the inside of the container 2 and can be implemented, for example, by means of a sponge. The transfer means 4 is slitted or notched in eight directions that originate at an opening 6 of the transfer means 4.

The eight slits/notches 6 do not extend all the way to the side walls of the container 2 and are meant to enable a medical implant to be pushed through the transfer means 4. The transfer means 4 thus has eight flexible segments that sweep over the surface of the medical implant when it is introduced and taken out or pulled out. The opening 6 can just as well be a circular recess whose diameter is smaller than the cross-section of the medical implants to be introduced. This ensures that the transfer means 4 sweeps over the entire surface of the medical implant and coats it in the process.

The transfer means 4 is manufactured from a flexible porous material. The material is hydrophilic. This ensures that it can be soaked easily with an aqueous liquid. Due to the hydrophobic properties of the container 2, an aqueous liquid that is being filled into the device 1 is taken up mainly by the transfer means 4. The transfer means 4 thereby easily gets soaked with an aqueous solution comprising an antibiotic.

The container 2 forms a hollow space 8 on the lower end of the device 1, which hollow space 8 is completely closed and closed off on the upper side by means of a membrane 10. The transfer means 4 is arranged on said membrane 10. A support ring 12 that is mobile along the longitudinal axis of the device 1 is arranged on the upper side of the transfer means 4. The transfer means 4 can be pressed together or compressed between the membrane 10 and the support ring 12.

It has an opening at the upper end of the container 2. An internal thread 14 is arranged on the upper side of the container 2 in the region of the opening. The support ring 12 cannot advance into the region of the internal thread 14 in the container 2, since the internal thread protrudes and thus blocks the path of the support ring. The support ring 12 is flat and approx. 1 mm thick or thinner, preferably 0.5 to 1 mm thick. The purpose of the support ring 12 is to keep the transfer means 4 inside the container 2. The support ring 12 can have a snap-in locking device (not shown) arranged on it such that the support ring 12 can be readily inserted into the container 2, but cannot fall out again.

A graduation of the container 2 separates the region for the transfer means 4 and the support ring 12 from hollow space 8. The opening of the container 2 is closed by means of a lid 16 that also serves as compressing facility for the transfer means 4. The lid 16 is cylindrical in shape on its outside and comprises an external thread 18 that engages the internal thread 14 of the container 2. In FIG. 1, the lid 16 is screwed deeply into the container 2. By this means, the support ring 12 is pressed downwards in the direction of the graduation of the container 2. For this purpose, the porous, elastic transfer means 4, and thus the pores present in the transfer means 4, is/are compressed.

A liquid can be filled into the container 2 through a tube-shaped feed-through 20 in the lid 16. The feed-through 20 in the present case is covered through a membrane 22 that can either be pulled off or punctured to fill device 1 with a liquid.

The lid 16 is subdivided into two parts by means of a divider wall 24. The lower region into which the feed-through 20 opens forms a hollow space in the lid 16 and/or device 1, in which ribs (not shown) are arranged that provide for distribution of a liquid filled into said hollow space and simultaneously can press onto the transfer means 4 and thus can contribute to the compression of the transfer means 4. The underside of the lid 16 could just as well be bordered by a perforated plate, whereby it is important that a liquid filled into the hollow space in the lid 16 is guided onto as much surface of the transfer means 4 as possible and that the flow to said surface is not impeded without need.

Two wings 28 are arranged on the upper side of the lid 16 and can be used to easily screw-down or open the lid 16 manually.

Figure 2:
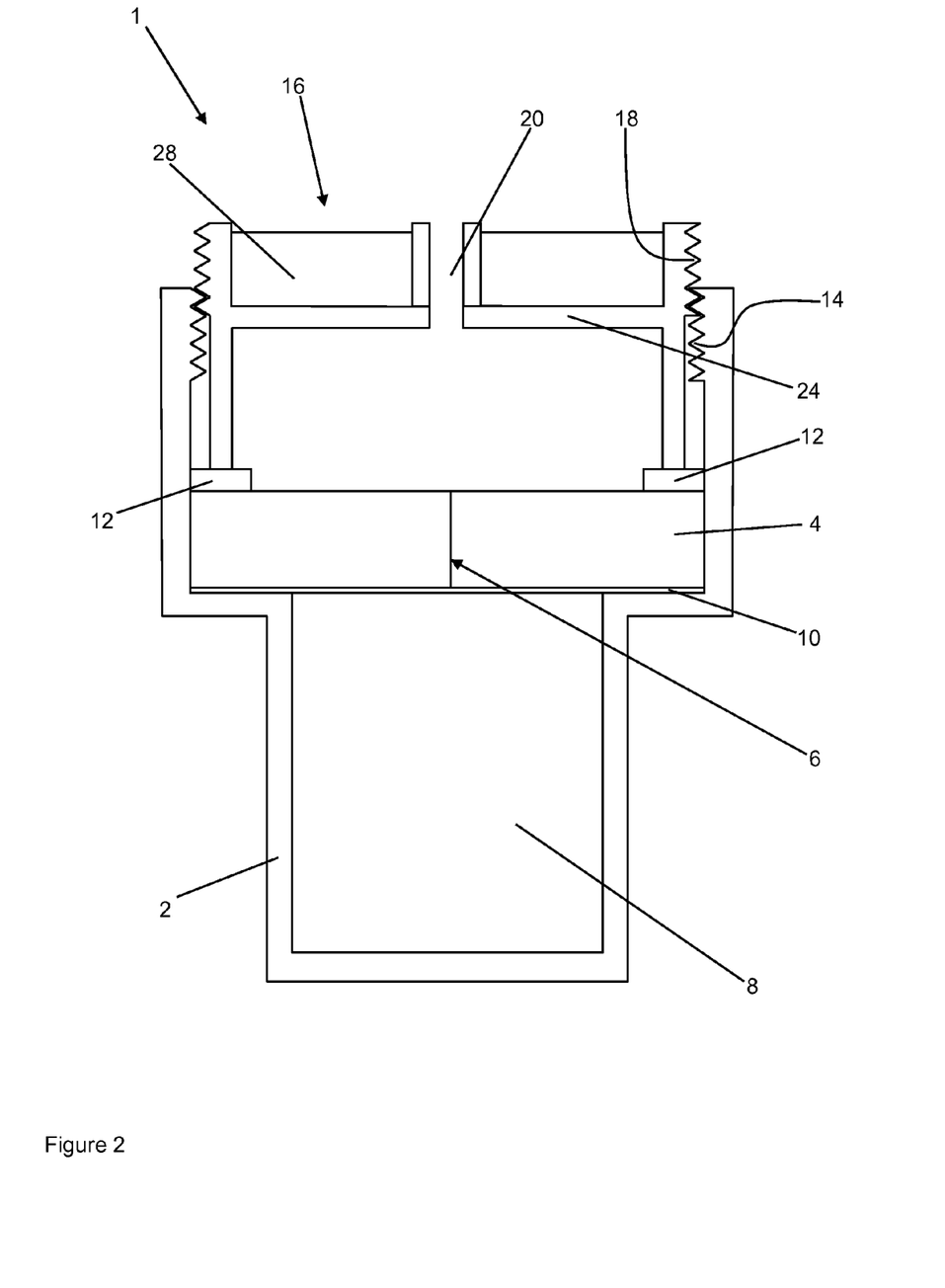
FIG. 2: shows a schematic cross-sectional view of the device according to the invention having a relaxed transfer means.

The device 1 shown can be used to carry out a method according to the invention. The membrane 22 on the feed-through 20 can be punctured or removed. Subsequently, an aqueous liquid comprising at least one pharmaceutical effective substance, preferably a coating solution or a coating suspension, is filled through the feed-through 20 into the hollow space in the lid 16 and thus into the container 2 and the device 1. This can be done, for example, with a syringe. The liquid cannot penetrate into the hollow space 8 that is closed through the membrane 10. Subsequently, the lid 16 is unscrewed from the container 2. The transfer means 4 expands while the lid is being unscrewed. The status, in which the lid 16 is largely screwed off, is shown in FIG. 2.

The expansion of the transfer means 4 re-opens the pores in the transfer means 4. The pores soak up liquid while they open up. Accordingly, the elastic spring force of the transfer means 4 is used to generate a pressure difference between the hollow spaces/pores in the transfer means 4 and the ambient pressure such that liquid is pressed and/or sucked into the hollow spaces, i.e. the pores of the transfer means 4. For this purpose, the device 1 should be held or supported such as to be approximately vertical such that the liquid in the hollow space of the lid 16 rests on the surface of the transfer means 4. For this purpose, a stand (not shown) can be arranged on the underside of the device 1.

By this means, the transfer means 4 is soaked with the aqueous liquid that contains at least one pharmaceutically effective substance and is to be used for coating a medical implant. The lid 16 can be removed for coating the medical implant just before use of the device 1.

A medical implant (not shown) is pushed through the opening of the container 2 and then encounters the transfer means 4. Owing to the pressure exerted on the transfer means 4 through the medical implant, the medical implant not only pushes through the breach 6 designed for this purpose in the transfer means 4, but also the liquid contained in the pores of the transfer means 4 is squeezed from the transfer means 4 and transferred to the surface of the medical implant. The medical implant punctures the membrane 10 and penetrates into the hollow space 8. The hollow space 8 takes up liquid droplets that drip down and is sufficiently large to take up the parts of the medical implant that have been pushed through the transfer means 4. The hollow space 8 can just as well contain a powder comprising a pharmaceutically effective substance into which the liquid-wetted medical implant is immersed whereby part of the powder adheres to the surface of the medical implant.

Once the surface of the medical implant has been coated, the medical implant is pulled out of the container 4. The coated surface of the medical implant can be pulled past a wiper (not shown) in the process. Excess liquid is wiped off the surface of the medical implant through the wiper and drips back into the container 2. The medical implant pulled out of the container 2 does not drip any longer then. These measures allow the liquid to be prevented from contaminating the surroundings. The medical implant coated with the liquid is then ready for use in a surgery.

Figure 3:
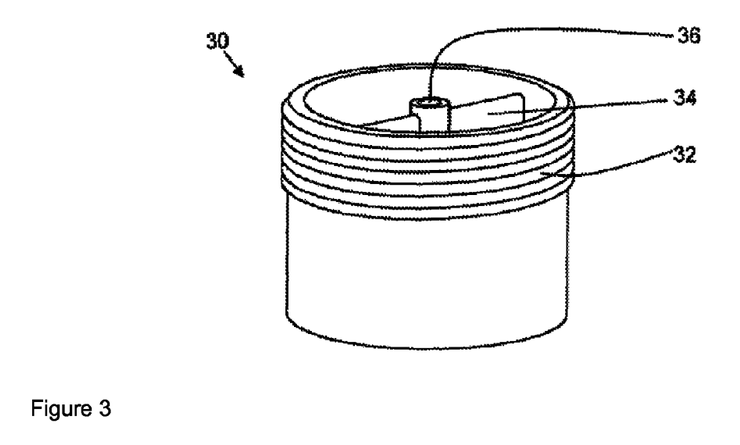
FIG. 3: shows a schematic perspective view of a lid acting as compressing facility for a device according to the invention.

FIG. 3 shows a schematic perspective view of a compressing facility in the from of a screw lid 30 for a device according to the invention. Made from plastic material, the lid 30 is cylinder-shaped and comprises an external thread 32 on its outside. To improve the handling, two wings 34 are arranged in the lid 30 such that a user can reach into the lid by hand and/or fingers and manually screw the lid 30 into the device (not shown) or unscrew the lid 30 from the device.

A tube serving as feed-through 36 is arranged in the middle of the lid 30 along the symmetry axis. The feed-through 36 preferably does not extend to the underside of the lid 30, but rather terminates above the lid. In the region of the lower edge of the external thread 32, a divider wall (not shown) is situated on the inside of the lid 30 which has only the feed-through 36 extend through it. The space underneath is intended to be filled up with the liquid for coating the medical implant.

Figure 4:
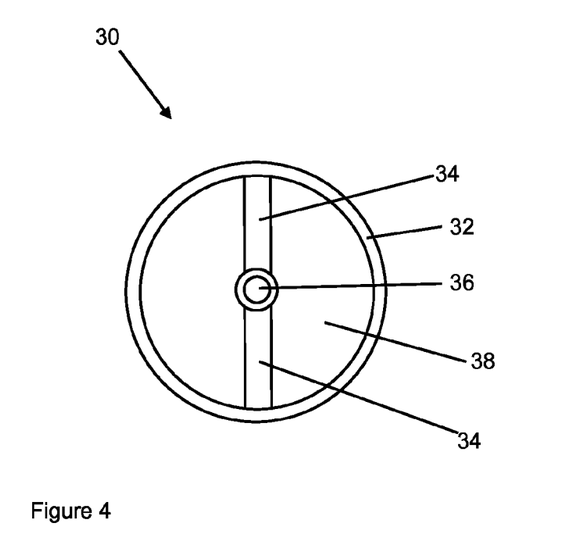
FIG. 4: shows a schematic top view of the upper side of a lid acting as compressing facility for a device according to the invention.

FIG. 4 shows the lid 30 according to FIG. 3 in a schematic top view from above. The divider wall 38 can be seen from above. The centric arrangement of the feed-through 36 in the lid 30 is also shown quite well.

Figure 5:
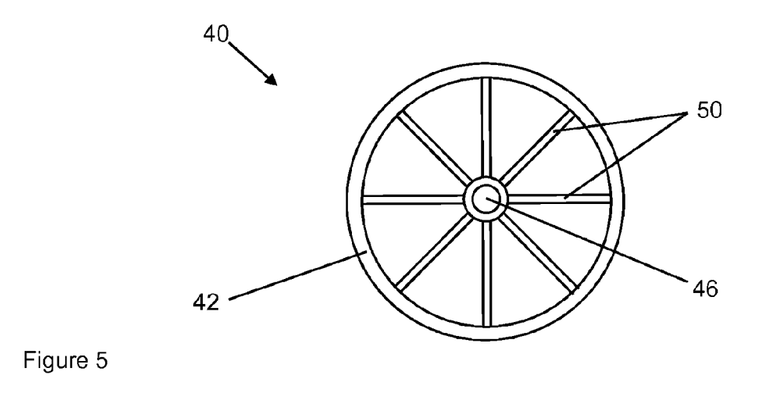
FIG. 5: shows a schematic top view of the underside of a lid acting as compressing facility for a device according to the invention.

FIG. 5 shows a schematic perspective top view onto the underside of a lid 40 acting as compressing facility. The walls 42 of the lid 40 have a cylindrical geometry. A feed-through 46 that extends through a divider wall 48 extends along the symmetry axis of the lid 40 in the region of the upper side up to a middle height level. The region on the underside of the divider wall 48 intended to form the hollow space in the lid 40 is subdivided into eight parts through ribs 50. The purpose of the ribs 50 is to distribute the liquid and compress the transfer means (not shown).

Figure 6:
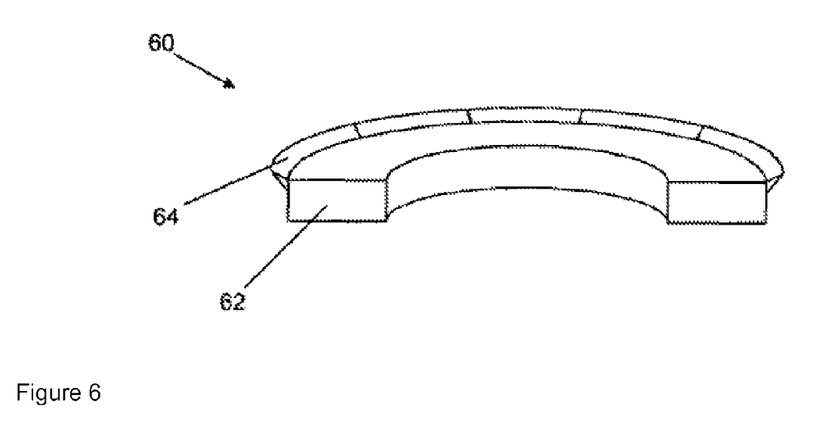
FIG. 6: shows a schematic perspective cross-sectional view of a support ring for a device according to the invention.

FIG. 6 shows a schematic perspective view of a support ring 60 that comprises a ring 62 and a segmented, mobile support device 64. The purpose of the support device 64 is to ensure that the support ring 60 can no longer be readily removed from the device when it is inserted into a medical coating device. For this purpose, the support device 64 can, for example, engage the lowest region of the internal thread 14 for the lid 16 according to FIG. 1 and FIG. 2.

Rather than using a lid 16, 30, 40 as compressing facility, an alternative compressing facility can just as well be used for compressing the transfer means 4. For example a cuff in the form of a broad band can be placed around a transfer means, whereby the cuff is pulled together and thus keeps the volume of the transfer means reduced. For this purpose, the cuff might comprise a screw device such that the circumference of the cuff and thus the volume can be enlarged slowly. The cuff would then be designed like a hose clip. Likewise, the cuff could just as well comprise a releasable lock that can be used to fully release and/or open the cuff allowing the volume of the transfer means to expand instantaneously. It is preferred in these cases for the transfer means to consist of a material whose elasticity allows only for non-sudden increase of the volume. This is to ensure that the pores of the transfer means are filled with liquid more homogeneously and more completely. Further refinements of compressing facilities, for example by means of the container and its geometry, are conceivable as well.

In the non-filled state, the lid 16, 30, 40 presses the elastic, porous transfer means 4 against the membrane 10. The pores are compressed at this time. Unscrewing or re-moving the lid 16, 30, 40 causes the elastic transfer means 4 to relax instantaneously and the coating solution or coating suspension situated on the surface of the transfer means 4 is sucked up into the enlarging pores synchronous to the increase of the volume of the transfer means 4.

According to the invention, in the non-filled state, the lid 16, 30, 40 is rotated by means of the thread 18, 32 in the direction of the elastic, open-porous transfer means 4 such that the same is compressed in such manner that the air is squeezed from a large part of the pores.

Accordingly, a method can be implemented in that the coating solution or coating suspension is filled into the opening 20, 36 of a screw lid 16, 30 compressing the elastic, open-porous transfer means 4 and in that the screw lid 16, 30 is subsequently being unscrewed out of the container 2, whereby the elastic, open-porous transfer means 4 relaxes while the screw lid 16, 30 is being unscrewed and enlarges its volume and soaks up the coating solution of coating suspension into the expanding pores. The screw lid 16, 30 is discarded once it is unscrewed.

The method is based on the elastic restoring force of the elastic, open-porous transfer means 4. The advantage of the method is that the transfer means 4 is automatically filled with the coating solution or coating suspension while the screw lid 16, 30 is being unscrewed. There is no need to squeeze the air from the pores in cumbersome manner.

Examples of the production of a liquid for a method according to the invention are presented in the following.

A total of 16.0 g gentamicin sulfate (Fujian Fukang Ltd.) were mixed with 4.0 ml pyrogen-free sterile water at room temperature. After stirring with a magnetic stirrer for 24 hours at room temperature, an oily-viscous yellowish solution had formed. This results in a coating solution containing gentamicin sulfate as liquid for coating a medical implant.

Production of a coating solution containing the two-component combination of gentamicin sulfate and clindamycin hydrochloride:

A total of 12.0 g gentamicin sulfate (Fujian Fukang Ltd.) were mixed with 4.0 g clindamycin hydrochloride (Sigma-Aldrich) and 4.0 ml pyrogen-free sterile water at room temperature. After stirring with a magnetic stirrer for 24 hours at room temperature, an oily-viscous yellowish solution had formed.

Production of a coating solution containing the three-component combination of gentamicin sulfate, clindamycin hydrochloride, and vancomycin hydochloride:

A total of 4.0 g gentamicin sulfate (Fujian Fukang Ltd.), 4.0 g clindamycin hydrochloride (Sigma-Aldrich), and 4.0 g vancomycin hydrochloride (Sigma-Aldrich) were mixed with 8.0 ml pyrogen-free sterile water at room temperature. After stirring with a magnetic stirrer for 24 hours at room temperature, a viscous yellowish solution had formed.

Using conventional 10 ml plastic syringes, 5 ml of each of the coating solutions of the examples given were drawn up and then the filled plastic syringes were used to inject 4 ml of the corresponding agent solution into a device according to the invention. Operation of the compressing facility and/or relaxation of the transfer means causes the agent solution to be soaked up by the porous transfer means.

Subsequently, customary Zweymüller hip prostheses were briefly dipped into a pre-filled device according to the invention until just before the end of the stem and then pulled out instantaneously. The Zweymüller hip endoprostheses are thus provided with a viscous film of the agent solution at the surface of the stem.

The features of the invention disclosed in the preceding description and in the claims, figures, and exemplary embodiments, can be essential for the implementation of the various embodiments of the invention both alone and in any combination.

LIST OF REFERENCE NUMBERS

1 Device
2 Container
4 Transfer means/sponge
6 Opening/slit in the transfer means
8—Hollow space in the container
10 Membrane
12, 60 Support ring
14 Internal thread
16, 30, 40 Lid/compressing facility
18, 32 External thread
20, 36, 46 Feed-through
22 Membrane
24, 38, 48 Divider wall
28, 34 Wing
42 Lid wall
50 Rib
62 Ring
64 Support device

We claim:

1. A method for coating, at least regions of, a medical implant, the method comprising:
    providing a medical implant;
    filling a device (1) with a liquid comprising at least one pharmaceutically active substance, wherein the device (1) comprises a hollow body having a closed end, an open end located opposite to the closed end, a compressing facility and a compressed, at least over regions thereof, elastic, porous transfer means (4) arranged at the open end of the hollow body;
    increasing a volume of the transfer means (4) by operating the compressing facility such that the transfer means expands outwardly away from the closed end of the hollow body, whereby the liquid is taken up at least partly into the pores of the transfer means (4); and
    subsequently transferring the liquid from the transfer means (4) to a medical implant surface to be coated.

2. The method according to claim 1, wherein the volume of the transfer means (4) is increased through relaxation and/or decompression of the transfer means (4).

3. The method according to claim 1, wherein the transfer means (4) is kept in the compressed state through the compressing facility (16, 30, 40).

4. The method according to claim 3, wherein a lid (16, 30, 40) having a thread (18, 32) is used as the compressing facility (16, 30, 40), whereby the thread (18, 32) engages a counter-thread (14) of the device (1), and that the volume of the transfer means (4) is increased by means of unscrewing the lid (16, 30, 40).

5. The method according to claim 1, wherein the liquid is filled into the device through at least one feed-through (20, 36, 46) in the device (1), right before transfer to the medical implant, whereby a previously closed feed-through (20, 36, 46) is openable through puncturing or removing a closure membrane (10).

6. The method according to claim 1, wherein the liquid is transferred from the transfer means (4) onto a medical implant surface to be coated by means of pushing the medical implant through one slit (6) or more slits and/or a recess (6) formed in the transfer means (4) and subsequently retracting, whereby excess of liquid is wiped off the medical implant during retraction.

7. The method according to claim 6, wherein the transfer means (4) is compressed, at least over regions thereof, while the medical implant is pushed through the transfer means, and at least part of the liquid is squeezed from the transfer means (4) and transferred to the surface of the medical implant.

8. The method according to claim 1, wherein an antibiotic or mixture of antibiotics is used as liquid.

9. The method according to claim 1, wherein a powder is applied to at least one wetted surface of the medical implant after transfer of the liquid to the medical implant, whereby the powder comprises at least one pharmaceutically active substance and is located in a hollow space between the transfer means and the closed end of the hollow body.

10. The method according to claim 1, wherein a coloured liquid is used such that the coated region of the medical implant is identified by colour, whereby the completeness of coating of the region to be coated is checkable by means of the colouration.

11. A device (1) for coating at least regions of a medical implant, the device (1) comprises:
 a hollow body having a closed end, an open end located opposite to the closed end of the hollow body;
 at least one transfer means (4), that is compressed, at least over regions thereof that are elastic and porous, arranged at the open end;
 a compressing facility, wherein the at least one transfer means is located between the compressing facility and the closed end of the hollow body; and
 a mobile support ring, located between the compressing facility and the at least one transfer means, maintains the at least one transfer means within the open end of the hollow body,
 wherein the at least one transfer means is configured to expand outwardly away from the closed end of the hollow body by operation of the compressing facility.

12. The device (1) according to claim 11, wherein the device (1) is a medical coating device (1).

13. The device (1) according to claim 11, whereby the transfer means (4) is maintained in a compressed state by means of the compressing facility (16, 30, 40) and a volume of the transfer means (4) is increasable through operating the compressing facility.

14. The device (1) according to claim 11, wherein the compressing facility (16, 30, 40) is a lid (16, 30, 40) having a thread (18, 32) that is screwed into the device (1), whereby the volume of the transfer means (4) is increasable through rotating and/or unscrewing the lid (16, 30, 40).

15. The device (1) according to claim 14, wherein the lid (16, 30, 40) comprises a feed-through (20, 36, 46) through which a liquid can be introduced into the open end of the hollow body of the device (1) in the region of the transfer means (4), whereby the feed-through (20, 36, 46) opens into a distributing facility by means of which the liquid can be distributed over at least regions of the surface of the transfer means (4), and the distributing facility comprises ribs (50) in a radial arrangement.

16. The device (1) according to claim 13, wherein the mobile support ring (12, 60) supports the at least one transfer means (4) on the inside of the device (1), independent of the compression of the transfer means (4), whereby the support ring (12, 60) comprises a locking device (64) which uses a limit stop of the device (1) to support the inserted support ring (12, 60), and thus the transfer means (4), in the device (1), limits the motion of the support ring (12, 60) in the device (1).

17. The device (1) according to claim 14, further comprising an opening at the open end of the hollow body for introduction and removal of the medical implant, whereby the opening is closed through the lid (16, 30, 40).

18. The device (1) according to claim 11, wherein the device (1) comprises a wiper that is arranged in the region of the open end of the hollow body.

19. The device (1) according to claim 11, further comprising:
 multiple transfer means (4) that each comprise at least one notch (6), whereby the arrangement of the transfer means (4) with respect to each other is such that the notches (6) are arranged offset with respect to each other.

20. The device (1) according to claim 19, wherein the transfer means (4) is a sponge, or multiple transfer means (4) are sponges, usable to transfer the liquid to the medical implant surface to be coated, whereby the sponge is, or sponges are, manufactured from a material having a hydrophilic surface, whereby the hollow body of the device is manufactured from a hydrophobic material.

21. The device (1) according to claim 11, wherein a hollow space (8) is arranged below the transfer means (4), whereby the transfer means (4) is arranged on a membrane (10) that is configured to be punctured and closes the inside of the hollow space (8).

22. A method for coating, at least regions of, a medical implant, the method comprising:
 providing a medical implant selected from the group consisting of a hip endoprosthese, a shoulder endoprosthese, an elbow prosthese, a marrow nail and an osteosynthesis plate;
 filling a device with a liquid comprising at least one pharmaceutically active substance, wherein the device comprises a compressed, at least over regions thereof, elastic, porous transfer means;
 increasing a volume of the transfer means, whereby the liquid is taken up at least partly into the pores of the transfer means; and
 subsequently transferring the liquid from the transfer means to a medical implant surface to be coated.

* * * * *